(12) United States Patent
Daines et al.

(10) Patent No.: US 6,486,211 B1
(45) Date of Patent: Nov. 26, 2002

(54) INDOLE COMPOUNDS

(75) Inventors: Robert A. Daines, Lansdale, PA (US); William Dennis Kingsbury, Phoenixville, PA (US); Israil Pendrak, Ambler, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 246 days.

(21) Appl. No.: 10/089,670

(22) PCT Filed: Oct. 2, 2000

(86) PCT No.: PCT/US00/29081

§ 371 (c)(1), (2), (4) Date: Apr. 2, 2002

(87) PCT Pub. No.: WO01/30755

PCT Pub. Date: May 3, 2001

Related U.S. Application Data

(60) Provisional application No. 60/161,134, filed on Oct. 22, 1999.

(51) Int. Cl.[7] ................ C07D 209/04; A61K 31/404
(52) U.S. Cl. ........................ 514/714; 548/491
(58) Field of Search ........................ 548/491; 514/714

(56) References Cited

U.S. PATENT DOCUMENTS 5,482,960 A    1/1996    Berryman et al.
5,684,032 A    11/1997    Elliot et al.

*Primary Examiner*—Alan L. Rotman
*Assistant Examiner*—Golam M. M. Shameem
(74) *Attorney, Agent, or Firm*—Soma G. Simon; Mary E. McCarthy; Charles M. Kinzig

(57) ABSTRACT

Novel indole derivatives, pharmaceutical compositions containing these compounds and their use as inhibitors of the fatty acid synthase FabH are disclosed.

5 Claims, No Drawings

INDOLE COMPOUNDS

This application is a 371 of PCT/US00/29081 Oct. 20, 2000 which claims benefit of Ser. No. 60/161,134 Oct. 22, 1999.

FIELD OF THE INVENTION

This invention relates to indole derivatives, pharmaceutical compositions containing these compounds and their use as inhibitors of the fatty acid synthase FabH and antibacterial agents.

BACKGROUND OF THE INVENTION

The pathway for the biosynthesis of saturated fatty acids is very similar in prokaryotes and eukaryotes. However, although the chemical reactions may not vary, the organization of the biosynthetic apparatus is very different. Vertebrates and yeasts possess type I fatty acid synthases (FASs) in which all of the enzymatic activities are encoded on one or two polypeptide chains, respectively. The acyl carrier protein (ACP) is an integral part of the complex. In contrast, in most bacterial and plant FASs (type II) each of the reactions are catalyzed by distinct monofunctional enzymes and the ACP is a discrete protein. Mycobacteria are unique in that they possess both type I and II FASs; the former is involved in basic fatty acid biosynthesis whereas the latter is involved in synthesis of complex cell envelope lipids such as mycolic acids. There therefore appears to be considerable potential for selective inhibition of the bacterial systems by broad spectrum antibacterial agents (Jackowski, S. 1992. In Emerging Targets in Antibacterial and Antifungal Chemotherapy. Ed. J. Sutcliffe & N. Georgopapadakou. Chapman & Hall, New York: Jackowski, S. et al. (1989). J. Biol. Chem. 264, 7624–7629.)

The first step in the biosynthetic cycle is the condensation of malonyl-ACP with acetyl-CoA by FabH. In subsequent rounds malonyl-ACP is condensed with the growing-chain acyl-ACP (FabB and FabF, synthases I and II respectively). The second step in the elongation cycle is ketoester reduction by NADPH-dependent β-ketoacyl-ACP reductase (FabG). Subsequent dehydration by β-hydroxyacyl-ACP dehydrase (either FabA or FabZ) leads to trans-2-enoyl-ACP which is in turn converted to acyl-ACP by NADH-dependent enoyl-ACP reductase (FabI). Further rounds of this cycle, adding two carbon atoms per cycle, eventually lead to palmitoyl-ACP whereupon the cycle is stopped largely due to feedback inhibition of FabH and I by palmitoyl-ACP (Heath. et al. (1996). J.Biol.Chem. 271, 1833–1836). Fab H is therefore a major biosynthetic enzyme which is also a key regulatory point in the overall synthetic pathway (Heath, R. J. and Rock. C. O. 1996. J.Biol.Chem. 271. 1833–1836; Heath, R. J. and Rock, C. O. 1996. J.Biol.Chem. 271, 10996–11000).

The antibiotic thiolactomycin has broad-spectrum antibacterial activity both in vivo and in vitro and has been shown to specifically inhibit all three condensing enzymes. It is non-toxic and does not inhibit mammalian FASs (Hayashi, T. et al.,1984. J. Antibiotics 37, 1456–1461. Miyakawa. S. et al., 1982. J. Antibiotics 35, 411–419; Nawata, Y et al., 1989. Acta Cryst. C45, 978–979; Noto, T. et at., 1982. J. Antibiotics 35, 401–410; Oishi, H. et al., 1982. J. Antibiotics 35, 391–396. Similarly, cerulenin is a potent inhibitor of FabB & F and is bactericidal but is toxic to eukaryotes because it competes for the fatty-acyl binding site common to both FAS types (D'Agnolo. G. et al.,1973. Biochim. Biophys. Acta. 326, 155–166). Extensive work with these inhibitors has proved that these enzymes are essential for viability. Little work has been carried out in Gram-positive bacteria.

There is an unmet need for developing new classes of antibiotic compounds that are not subject to existing resistance mechanisms. No marketed antibiotics are targeted against fatty acid biosynthesis, therefore it is unlikely that novel antibiotics of this type would be rendered inactive by known antibiotic resistance mechanisms. Moreover, this is a potentially broad spectrum target. Therefore, FabH inhibitors would serve to meet this unmet need.

SUMMARY OF THE INVENTION

This invention comprises indole derivatives and pharmaceutical compositions containing these compounds, and their use as FabH inhibitors which are useful as antibiotics for the treatment of Gram positive and Gram negative bacterial infections. This invention further constitutes a method for treatment of a Gram negative or Gram positive bacterial infection in an animal, including humans, which comprises administering to an animal in need thereof, an effective amount of a compound of this invention.

DETAILED DESCRIPTION OF THE INVENTION

The compounds of this invention are represented by Formula (I):

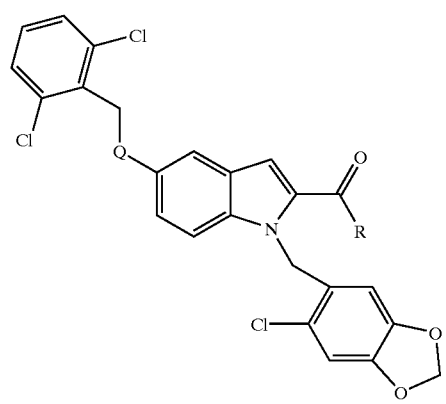

wherein:

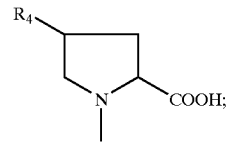

R is —N($R_1$)—C($R_2$)H—$CO_2$H or
Q is O or $CH_2$;
$R_1$ is hydrogen or $C_{1-5}$ alkyl;
$R_2$ is hydrogen, $C_{1-5}$alkyl, $(CH_2)_nR_3$, CH(OH)$CH_3$;
$R_3$ is OH, $CO_2R_1$, $CONH_2$, $NH_2$, CH(OH)$(CH_2)_n NH_3$, NH—C(NH)$NH_2$,—SH, —$SCH_3$ or phenyl which may be substituted or unsubstituted by OH:
$R_4$ is hydrogen or OH;
n is an integer from 1 to 5;
or a pharmaceutically acceptable salt thereof.

Also included in the invention are pharmaceutically acceptable salt complexes.

When used herein the terms 'alkyl' includes straight and branched chain groups containing from 1 to 5 carbon atoms, such as methyl, ethyl, propyl and t-butyl.

The compounds of this invention may contain one or more asymmetric carbon atoms and may exist in racemic and optically active forms. The compounds may be in the D or L form. All of these compounds and diastereomers are contemplated to be within the scope of the present invention.

Some of the compounds of this invention may be crystallised or recrystallised from solvents such as organic solvents. In such cases solvates may be formned. This invention includes within its scope stoichiometric solvates including hydrates as well as compounds containing variable amounts of water that may be produced by processes such as lyophilisation. All polymorhphs are also included.

Since the antibiotic compounds of the invention are intended for use in pharmaceutical compositions it will readily be understood that they are each provided in substantially pure form, for example at least 60% pure, more suitably at least 75% pure and preferably at least 85%, especially at least 95% pure, particularly at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 49% of a compound of the formula (I) or salt thereof.

Preferred compounds have Q as O and R is alanyl, prolyl, valyl, isoleucyl or leucyl. The L isomers are preferred. Especially preferred is prolyl. n-methyl alanyl, and leucyl.

Preferred compounds are:

N-methyl-1-(6-chloro-3,4-methylenedioxybenzyl)-5-(2,6-dichlorobenzyloxy)indole-2-carboxy-L-alanine amide:
1-(6-chloro-3,4-methylenedioxybenzyl)-5-(2,6-dichlorobenzyloxy)indole-2-carboxy-L-proline amide;
1-(6-chloro-3,4-methylenedioxybenzyl)-5-(2,6-dichlorobenzyloxy)indole-2-carboxy-L-alanine amide;
(6-chloro-3,4-methylenedioxybenzyl)-5-(2,6-dichlorobenzyloxy)indole-2-carboxy-L-leucine amide;
1-(6-chloro-3,4-methylenedioxybenzyl)-5-(2,6-dichlorobenzyloxy)indole-2-carboxy-L-valine amide: and
1-(6-chloro-3,4-methylenedioxybenzyl)-5-(2,6-dichlorobenzyloxy)indole-2-carboxy-L-isoleucine amide.

Compounds of the formula I wherein Q is O are prepared by the method described in Schemes 1 and 2.

Scheme 1

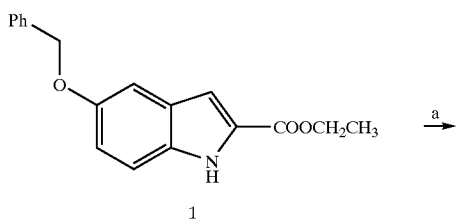

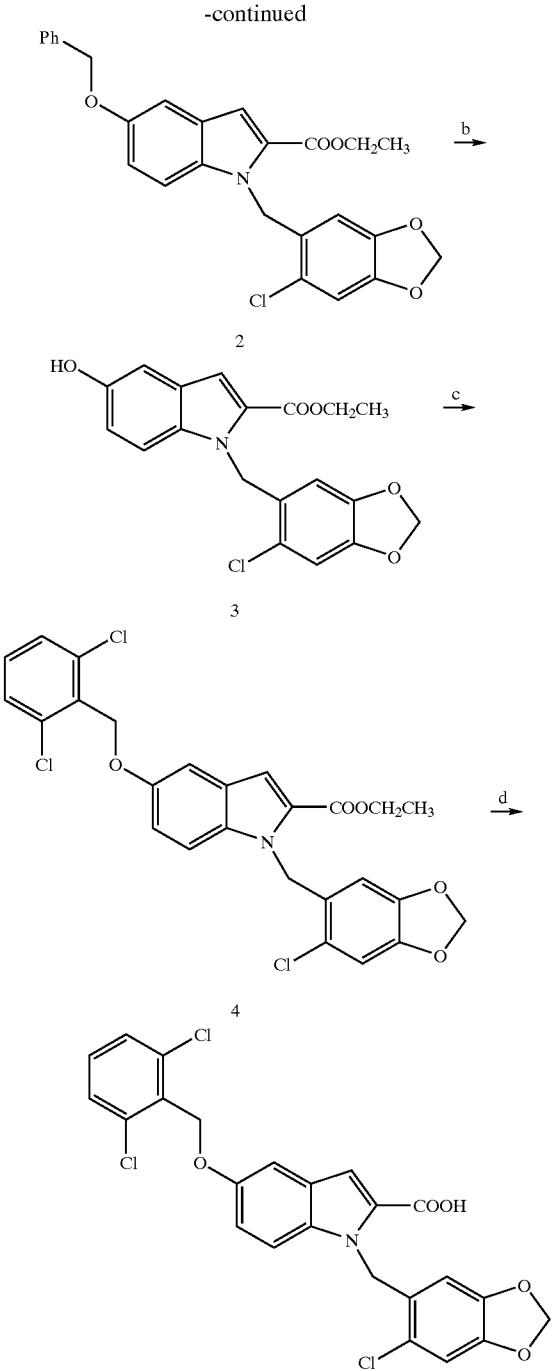

a) 6-chloropiperonyl chloride, NaH, DMF; b) 10% Pd/C, $H_2$, EtOAc; c) 2,6 dichlorobenzyl bromide, NaH, DMF; d) KOH, EtOH/THF, reflux Indole ester 1-Scheme-1(Aldrich) and a base (such as sodium hydride) are treated with a solvent (such as DMF) and then 6-chloropiperonyl chloride is added and stirred (6 hours to 30 hours, preferably 20 hours) to yield 2-Scheme-1. 2-Scheme-1 is dissolved in a solvent (such as ethyl acetate) and treated with 10% Palladium on charcoal and the resulting mixture shaken (6 hours to 30 hours, preferably 20 hours) to yield 3-Scheme-1. Alkylation of 3-Scheme-1 with 2,6-dichlorobenzyl bromide using a base (such as sodium hydride) in a solvent (such as DMF) provides 4-Scheme-1. Saponification of 4-Scheme-1 with a base (such as potassium hydroxide) in a solvent (such as ethanol and tetrahydrofuran) provides 5-Scheme-1.

Scheme 2

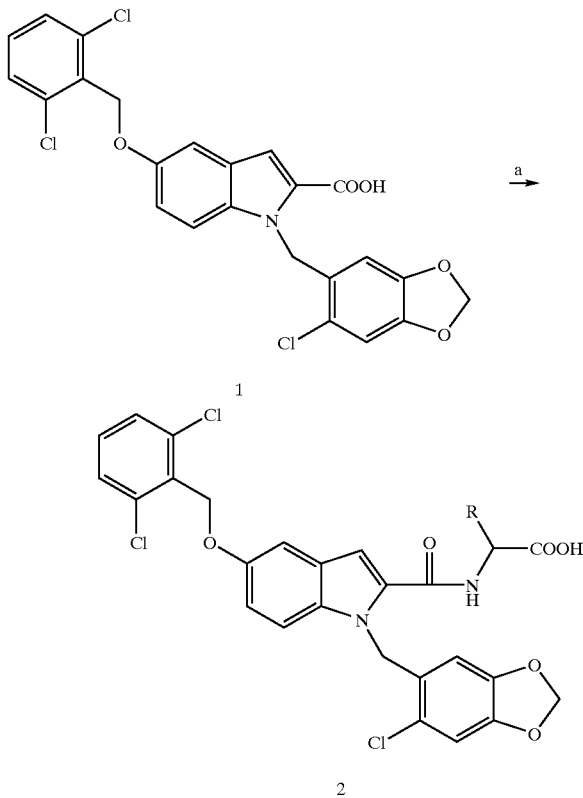

a) 1. amino acid ester hydrochloride, BOP, TEA, CH$_2$Cl$_2$; 2. LiOH, THF/MeOH 1-Scheme-2 is treated with an amino acid hydrochloride ester (such as L-alanine ethyl ester hydrochloride) and a coupling agent (such as BOP Reagent. Aldrich) and a base (such as triethyl amine) in a solvent (such as methylene chloride). Saponification of the resulting ester with a base (such as lithium hydroxide) in a solvent (such as methanol and THF) yields 2-Scheme-2.

Biological Assay

FabH Inhibition

The assay is designed to measure IC50s against Streptococcus pneumoniae β-ketoacyl-ACP synthase III (FabH). Substrates malonyl-ACP, [14 C]-acetyl-coA are combined with FabH to produce [14C]-acetoacetyl-ACP.

| Conditions of assay: | |
|---|---|
| sodium phosphate pH 7.0 | 100 mM |
| beta-mercaptoethanol | 1 mM |
| malonyl acyl carrier protein | 20 uM |
| acetyl coenzymeA | 70 uM |
| [1–14C] acetyl coenzyme-A | 5 uM |
| FabH | 1–16 nM |
| Total reaction volume is 50 ul. | |

1) Compile all reagents minus enzyme and aliquot onto a 96 well plate already containing inhibitors.
2) Dilute FabH into assay buffer with 1 mM beta-mercaptoethanol and add to the plate to start the reaction. and incubate at 37C. for 40 minutes.
3) Stop reactions with 150ul 10%TCA.
4) Pre-wet GF/C filter mat with 10%TCA, filter stopped reactions, rinse wells with 150 ul of 10%TCA twice and filter.
5) Oven dry filter mat at 60C., seal filter mat in a clear plastic bag, add Betaplate scintillation cocktail and count with Wallac Microbeta liquid scintillation counter.

Antimicrobial Activity Assay

Whole-cell antimicrobial activity was determined by broth microdilution using the National Committee for Clinical Laboratory Standards (NCCLS) recommended procedure, Document M7-A4. "Methods for Dilution Susceptibility Tests for Bacteria that Grow Aerobically" (incorporated by reference herein). The compound was tested in serial two-fold dilutions ranging from 0.06 to 64 mcg/ml. A panel of 12 strains were evaluated in the assay. This panel consisted of the following laboratory strains: Staphylococcus aureus Oxford, Streptococcus pneumoniae R6. Streptococcus pyogenes CN10, Enterococcus faecalis I, Haemophilus influenzae Q 1. Escherichia coli DC0, E. coli ESS. E. coli 7623 (AcrAB$^+$) E. coli 120 (AcrAB–) Klebsiella pneumoniae E70, Pseudomonas aeruginosa K799wt and Candida albicans GRI 681. The minimum inhibitory concentration (MIC) was determined as the lowest concentration of compound that inhibited visible growth. A mirror reader was used to assist in determining the MIC endpoint.

The present invention also provides a pharmaceutical composition which comprises a compound of formula (I) or a pharmaceutically acceptable salt or in vivo hydrolysable ester thereof and a pharmaceutically acceptable carrier. The compositions of the invention include those in a form adapted for oral, topical or parenteral use and may be used for the treatment of bacterial infection in mammals including humans.

The antibiotic compounds according to the invention may be formulated for administration in any convenient way for use in human or veterinary medicine, by analogy with other antibiotics.

The composition may be formulated for administration by any route, such as oral, topical or parenteral, especially oral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form. and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing. The solution preferably contains a buffer (such as phosphate) to keep the pH in the range of about 3.5 to 7. DMSO or alcoholic solvents may also be present (at concentrations such as 0.01 to 10 mL/liter) to aid solubility and penetration of the compound of Formula (I).

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 1 to 140 mg/kg of body weight, depending on the route and frequency of administration..

No unacceptable toxicological effects are expected when a compound of formula (I) or a pharmaceutically acceptable salt or in vivo hydrolysable ester thereof is administered in the above-mentioned dosage range.

The compound of formula (I) may be the sole therapeutic agent in the compositions of the invention or a combination with other antibiotics or compounds which enhance the antibacterial activity of a compound of formula (I)may be employed.

The antibiotic compounds of the present invention are active against a wide range of organisms including both Gram-negative organisms such as *Escherichia coli* and *Klebsiella pneumoniae* and Gram-positive organisms such as *Staphylococcus aureus, Streptococcus pneumoniae, Enterococcus faecalis* and *Enterococcus faecium,* including isolates resistant to existing antibiotics.

The following Examples illustrate the preparation of compounds of the invention and intermediates thereto.

EXAMPLE 1

Preparation of 1-(6-chloro-3 4-methylenedioxybenzyl)-5-(2,6-dichlorobenzyloxy) indole-2-carboxy-L-proline amide a) Methyl ester of 1-(6-chloro-3,4-methylenedioxybenzyl)-5-(2,6-dichlorobenzyloxy)indole-2-carboxy-L-proline amide.

To a solution of 1-(6-chloro-3,4-methylenedioxybenzyl)-5-(2,6-dichlorobenzyloxy)indole-2-carboxylic acid (200 mg, 0.4 mmol) in methylene chloride (10mL) was added benzotriazol-1-yloxytris(dimethyamino) phosphoniumhexafluorophosphate (BOP) (0.134g, 0.45 mmol). The resulting mixture was shaken at room temperature for 5 min. (L)-H-Proline-methyl ester hydrochloride (79 mg, 0.42 mmol) was added alone with triethylamine (1.2 mL, 8.6 mmol). The resulting mixture was shaken at room temperature for 24 h. Methylene chloride (10 mL) was added and the organic layer was washed with $NaHCO_3$, $H_2O$, brine, dried ($MgSO_4$), filtered, and concentrated in vacuum to give an oil. The oil was purified by flash chromatography (silica gel, 30–80% EtOAc/hexane) to yield the title compound as a foam (97 mg, 41%). MS (ES+) m/e 616.8 $[M+H]^+$.

b) 1-(6-chloro- 3,4-methylenedioxybenzyl)-5-(2,6-dichlorobenzyloxy)indole-2-carboxy-L-proline amide.

To a solution of Methyl ester of 1-(6-chloro-3,4-methylenedioxybenzyl)-5-(2,6-dichlorobenzyloxy)indole-2-carboxy-L-proline amide (62 mg, 0.1 mmol) in THF (10 mL) and MeOH (10 mL) was added LiOH (10 mL, 3N aqueous solution). The resulting mixture was stirred at room temperature for 4 h. The solvent was removed in vacuum and the resulting mixture extracted with EtOAc. The organic layer was washed with $H_2O$, brine, dried ($MgSO_4$), filtered, and concentrated in vacuum to give a title compound as a solid (52.8 mg, 87%). MS (ES+) m/e 602.8 $[M+H]^+$.

EXAMPLE 2

Preparation of 1-(6-chloro-3,4-methylenedioxybenzyl)-5-(2,6-dichlorobenzyloxy) indole-2-carboxy-L-phenylalanine amide Following the procedure of Example 1 (a–b) except substituting (L)-H-Phenylalanine-methyl ester hydrochloride for (L)-H-Proline-methyl ester hydrochloride the title compound was prepared as a solid (90 mg, 50%). MS (ES+) m/e 652.8 $[M+H]^+$.

EXAMPLE 3

Preparation of 1-(6-chloro-3,4-methylenedioxybenzyl)-5-(2,6-dichlorobenzyloxy)indole-2-carboxy-L-serine amide.

Following the procedure of Example 1 (a–b) except substituting (L)-H-Serine-methyl ester hydrochloride for (L)-H-Proline-methyl ester hydrochloride the title compound was prepared as a solid (85 mg, 49%). MS (ES+) m/e 592.6 $[M+H]^+$.

EXAMPLE 4

Preparation of 1-(6-chloro-3,4-methylenedioxybenzyl)-5-(2,6-dichlorobenzyloxy) indole-2-carboxy-L-alanine amide.

Following the procedure of Example 1 (a–b) except substituting (L)-H-Alanine-methyl ester hydrochloride for (L)-H-Proline-methyl) ester hydrochloride the title compound was prepared as a solid (138 mg, 59%). MS (ES+) m/e 576.8 $[M+H]^+$.

EXAMPLE 5

Preparation of 1-(6-chloro-3,4-methylenedioxybenzyl)-5-(2,6-dichlorobenzyloxy) indole-2-carboxy-L-leucine amide.

Following the procedure of Example 1 (a–b) except substituting (L)-H-Leucine-methyl ester hydrochloride for (L)-H-Proline-methyl ester hydrochloride the title compound was prepared as a solid (74.4 mg, 65%). MS (ES+) m/e 618.9 [M+H]$^+$.

EXAMPLE 6

Preparation of 1-(6-chloro-3,4-methylenedioxybenzyl)-5-(2,6-dichlorobenzyloxy) indole-2-carboxy-L-valine amide.

Following the procedure of Example 1 (a–b) except substituting (L)-H-Valine-methyl ester hydrochloride for (L)-H-Proline-methyl ester hydrochloride the title compound was prepared as a solid (74.4 mg, 65%). MS (ES+) m/e604.8 [M+H]$^+$.

EXAMPLE 7

Preparation of 1-(6-chloro-3,4-methylenedioxybenzyl)-5-(2,6-dichlorobenzyloxy) indole-2-carboxy-L-Isoleucine amide.

Following the procedure of Example 1 (a) except substituting (L)-H-Isoleucine-tert-butyl ester hydrochloride for (L)-H-Proline-methyl ester hydrochloride and subsequent hydrolysis of tert-butyl ester with trifluriacetic acid in CH$_2$Cl$_2$ the title compound was prepared as a solid (44.3 mg, 35%). MS (ES+) m/e618.9 [M+H]$^+$.

EXAMPLE 8

Preparation of N-methyl-1-(6-chloro-3,4-methylenedioxybenzyl)-5-(2,6-dichlorobenzyloxy )indole-2-carboxy-L-alanine amide.

a) N-Methyl-L-alanine-methyl ester hydrochloride.

To a solution of N-Methyl-L-alanine (0.2g, 2 mmol) in MeOH (5 mL) was bubbled HCl (gas) for 2 min. The resulting mixture was stirred at room temperature for 24h. The solvent was removed in vacuum to give a title compound as a solid (0.38 mg. 100%). MS (ES+) m/e 118[M+H]$^+$.

b) Methyl ester of N-Methyl-1-(6-chloro-3,4-methylenedioxybenzyl)-5-(2,6-dichlorobenzyloxy) indole-2-carboxy-L-proline amide.

To a solution of 1-(6-chloro-3,4-methylenedioxybenzyl)-5-(2,6-dichlorobenzyloxy)indole-2-carboxylic acid (200 mg, 0.4 mmol) in methylene chloride (10mL) was added bromo-tris-pyrrolidino-phosphonium hexafluorophosphate (PyBroP) (0.2 g, 0.45 mmol). The resulting mixture was shaken at room temperature for 5 min. N-Methyl-L-alanine-methyl ester hydrochloride. (66 mg. 0.42 mmol) was added alone with triethylamine (1.2 mL, 8.6 mmol). The resulting mixture was shaken at room temperature for 24 h. Methylene chloride (10 mL) was added and the organic layer was washed with NaHCO$_3$, H$_2$O, brine, dried (MgSO$_4$), filtered, and concentrated in vacuum to give an oil. The oil was purified by flash chromatography (silica gel, 30–80% EtOAc/hexane) to yield the title compound as a foam (35 mg 41%). MS (ES+) m/e 604.6 [M+H]$^+$. c) N-Methyl-1-(6-chloro-3,4-methylenedioxybenzyl)-5-(2,6-dichlorobenzyloxy)indole-2-carboxy-L-alanine amide.

To a solution of Methyl ester of N-Methyl-1-(6-chloro-3,4-methylenedioxybenzyl)-5-(2,6-dichlorobenzyloxy)indole-2-carboxy-L-alanine amide (34 mg, 0.05 mmol) in THF (5 mL) and MeOH (5 mL) was added LiOH (5 mL, 3N aqueous solution). The resulting mixture was stirred at room temperature for 4h. The solvent was removed in vacuum and the resulting mixture extracted with EtOAc. The organic layer was washed with H$_2$O, brine, dried (MgSO$_4$), filtered, and concentrated in vacuum to give a title compound as a foam (29.1 mg, 89%). MS (ES+) m/e 590.8 [M+H]$^+$.

What is claimed is:

1. A compound of formula (I)

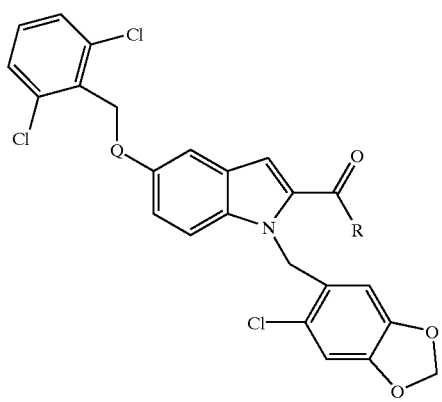

wherein:

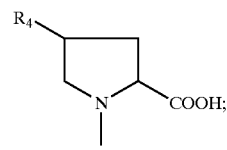

R is —N(R$_1$)—C(R$_2$)H—CO$_2$H or
Q is O or CH$_1$; and
R$_1$ is Hydrogen or C$_{1-5}$ alkyl;
R$_2$ is Hydrogen, C$_{1-5}$alkyl, (CH$_2$)$_n$R$_3$, CH(OH)CH$_3$;
R$_3$ is OH, CO$_2$R$_1$, CONH$_2$, NH$_2$, CH(OH)(CH$_2$)$_n$NH$_3$, NH—C(NH)NH$_2$, phenyl substituted or unsubstituted by OH, —SH, or —SCH$_3$;
n is an integer from 1 to 5,
or a pharmaceutically acceptable salt thereof.

2. A compound of claim 1 wherein Q is oxygen and R is alanyl, prolyl, valyl, isoleucyl, N-methyl alanyl, or leucyl.

3. A compound of claim 1 selected from the group consisting of:
N-methyl-1-(6-chloro-3,4-methylenedioxybenzyl)-5-(2,6-dichlorobenzyloxy)indole-2-carboxy-L-alanine amide;
1-(6-chloro-3,4-methylenedioxybenzyl)-5-(2,6-dichlorobenzyloxy)indole-2-carboxy-L-proline amide;
1-(6-chloro-3,4-methylenedioxybenzyl)-5-(2,6-dichlorobenzyloxy)indole-2-carboxy-L-alanine amide;
(6-chloro-3,4-methylenedioxybenzyl)-5-(2,6-dichlorobenzyloxy)indole-2-carboxy-L-leucine amide;
1-(6-chloro-3,4-methylenedioxybenzyl)-5-(2,6-dichlorobenzyloxy)indole-2-carboxy-L-valine amide; and
1-(6-chloro-3,4-methylenedioxybenzyl)-5-(2,6-dichlorobenzyloxy)indole-2-carboxy-L-isoleucine amide.

4. A pharmaceutical composition which comprises an effective amount of compound according to claim 1 and a pharmaceutically acceptable carrier.

5. A method of treating bacterial infections by administering to a patient in need thereof an effective amount of a compound of claim 1.

* * * * *